US009220473B2

(12) United States Patent
Blumhagen et al.

(10) Patent No.: US 9,220,473 B2
(45) Date of Patent: Dec. 29, 2015

(54) METHOD FOR CALCULATING A VALUE OF AN ABSORPTION PARAMETER IN POSITRON EMISSION TOMOGRAPHY

(71) Applicants: Jan Ole Blumhagen, Erlangen (DE); Matthias Fenchel, Erlangen (DE); Ralf Ladebeck, Erlangen (DE)

(72) Inventors: Jan Ole Blumhagen, Erlangen (DE); Matthias Fenchel, Erlangen (DE); Ralf Ladebeck, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 188 days.

(21) Appl. No.: 13/747,756

(22) Filed: Jan. 23, 2013

(65) Prior Publication Data
US 2013/0197349 A1 Aug. 1, 2013

(30) Foreign Application Priority Data

Feb. 1, 2012 (DE) .......................... 10 2012 201 412

(51) Int. Cl.
*A61B 5/05* (2006.01)
*A61B 6/00* (2006.01)
(Continued)

(52) U.S. Cl.
CPC ............. *A61B 6/5247* (2013.01); *A61B 5/0035* (2013.01); *A61B 5/0037* (2013.01);
(Continued)

(58) Field of Classification Search
CPC ...... A61B 6/5247; A61B 6/037; A61B 6/466; A61B 6/4417; A61B 5/0035; A61B 5/4872; A61B 5/4875; A61B 5/0555; A61B 5/72
USPC .................................................. 600/411, 415
See application file for complete search history.

(56) References Cited

U.S. PATENT DOCUMENTS

2010/0010757 A1 1/2010 Schmidt
2011/0015904 A1 1/2011 Fenchel et al.
(Continued)

FOREIGN PATENT DOCUMENTS

CN 101953693 A 1/2011
DE 102008032996 A1 1/2010
DE 102009048302 A1 4/2011

OTHER PUBLICATIONS

Hoffmann et al., MRI-Based Attenuation Correction for Whole-Body PET/MRI: Quantitative Evaluation of Segmentation and Atlas-Based Methods, The Journal of Nuclear Medicine, vol. 52, No. 9, Sep. 2011.*

(Continued)

*Primary Examiner* — Bo J Peng
(74) *Attorney, Agent, or Firm* — Harness, Dickey & Pierce, P.L.C.

(57) ABSTRACT

A method is disclosed for calculating a spatially resolved value of an absorption parameter for a positron emission tomography (PET) scan of an examination object via magnetic resonance tomography (MRT). Magnetic resonance data is acquired within a first region lying within a field of view of a magnetic resonance system and within a second region bordering on the first and lying at the edge of the field of view. The method includes the spatially resolved calculation of a first value of the absorption parameter from the first MR data within the first region and of a second value from the second MR data within the second region. A three-dimensional parameter map is obtained from the first value. This parameter map is extended by the second value such that within the first region and the second region the parameter map has the value of the absorption parameter in spatially resolved form.

21 Claims, 11 Drawing Sheets

(51) Int. Cl.
*A61B 5/00* (2006.01)
*A61B 6/03* (2006.01)
*A61B 5/055* (2006.01)
*G01R 33/48* (2006.01)

(52) U.S. Cl.
CPC .............. *A61B 5/055* (2013.01); *A61B 5/0555* (2013.01); *A61B 5/72* (2013.01); *A61B 6/037* (2013.01); *A61B 6/466* (2013.01); *A61B 6/5217* (2013.01); *G01R 33/481* (2013.01); *A61B 5/4872* (2013.01); *A61B 5/4875* (2013.01); *A61B 6/4417* (2013.01); *A61B 6/463* (2013.01)

(56) References Cited

U.S. PATENT DOCUMENTS

| | | | |
|---|---|---|---|
| 2011/0080168 A1* | 4/2011 | Fenchel et al. | 324/309 |
| 2011/0103669 A1 | 5/2011 | Michel et al. | |
| 2012/0056621 A1 | 3/2012 | Blumhagen et al. | |
| 2012/0235680 A1 | 9/2012 | Blumhagen et al. | |

OTHER PUBLICATIONS

Hu et al., Advancements in molecular medicine, Philips Ingenuity TF PET/MR attenuation correction, 2011 Koninklijke Philips Electronics N.V.*

Hu et al., MR-based Attenuation Correction for a Whole-body Sequential PET/MR System, 2009 IEEE Nuclear Science Symposium Conference Record, 3508-3512.*

G. Delso et al. "The effect of limited MR field of view in MR/PET attenuation correction" in Med. Phys. 37(2010), pp. 2804-2812; Others; 2010.

J. Nuyts et al. "Completion of a Truncated Attenuation image from the Attenuated PET Emission Data" in IEEE Nucl. Sci. Symp. Conf. Record 2010; Others; 2010.

German Priority Document for DE 10 2012 201 412.8 (Not Yet Published).

Chinese Office Action dated Aug. 6, 2015 for corresponding CN Application No. 201310041350.8.

* cited by examiner

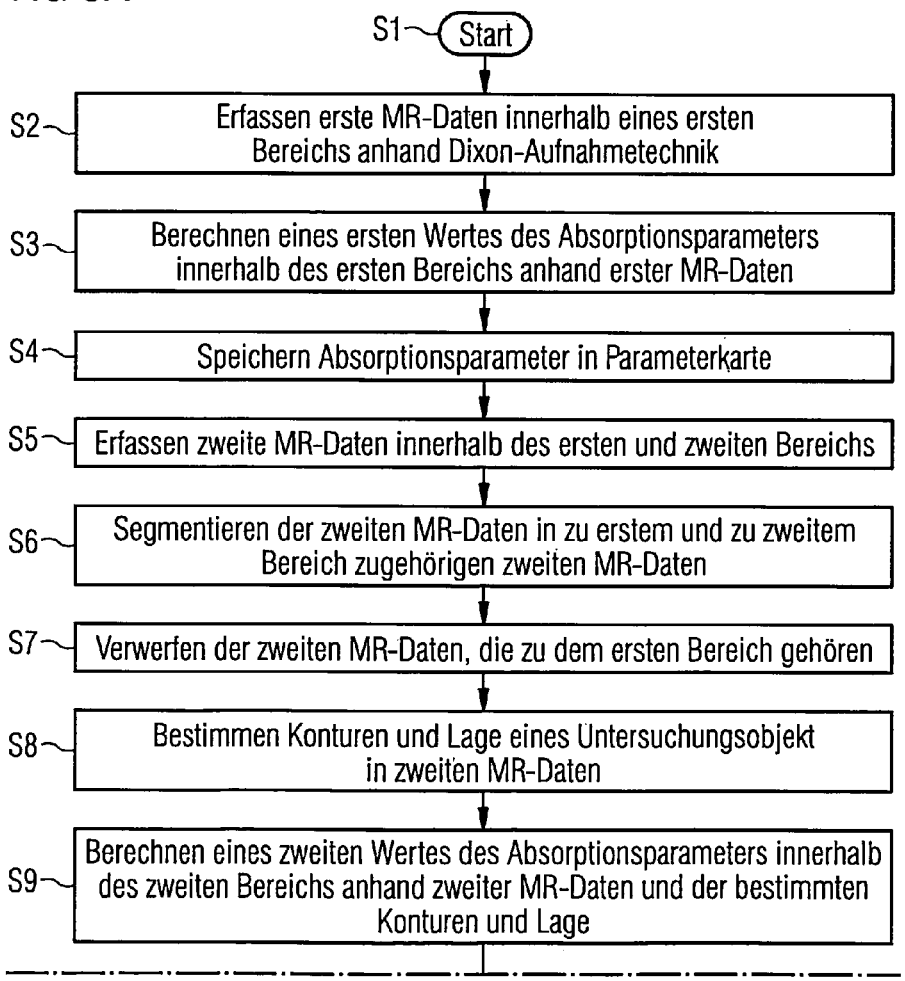

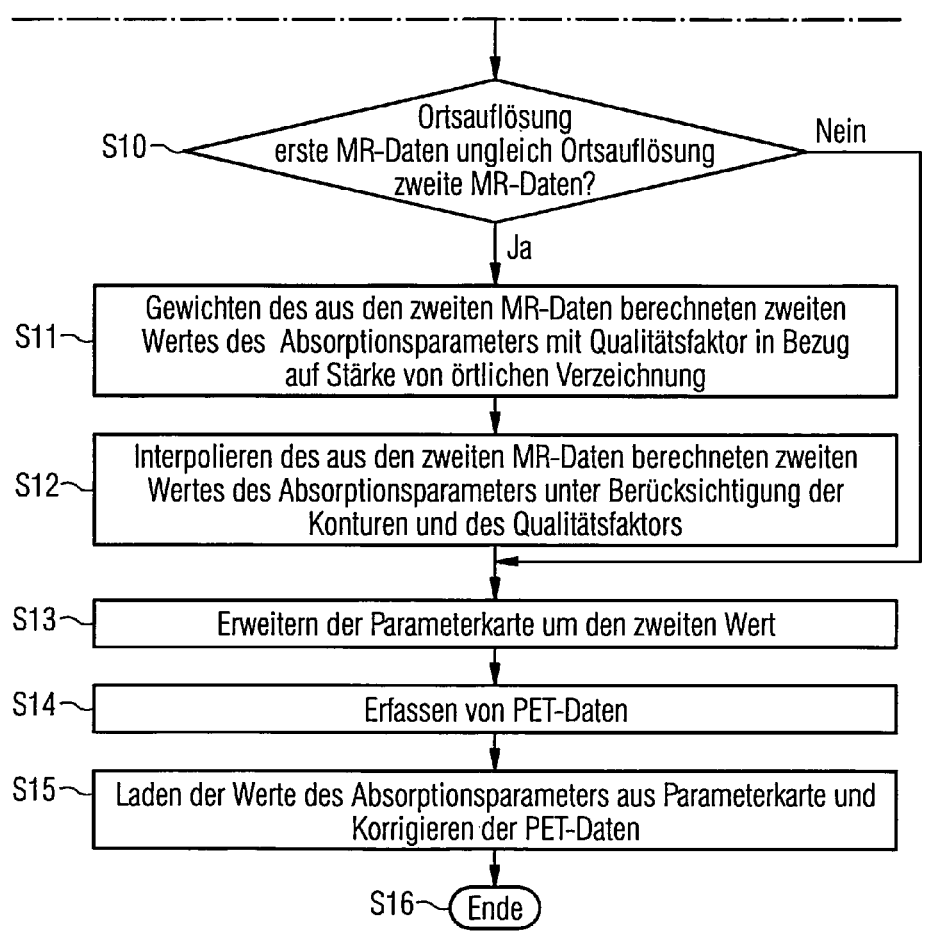

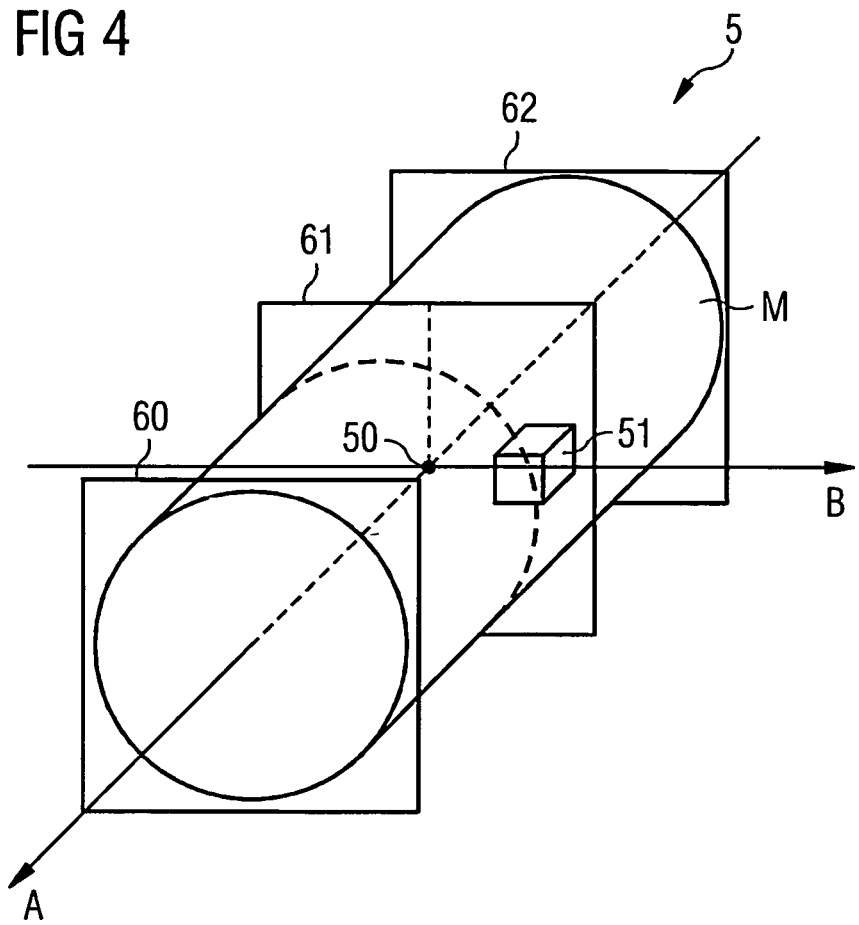

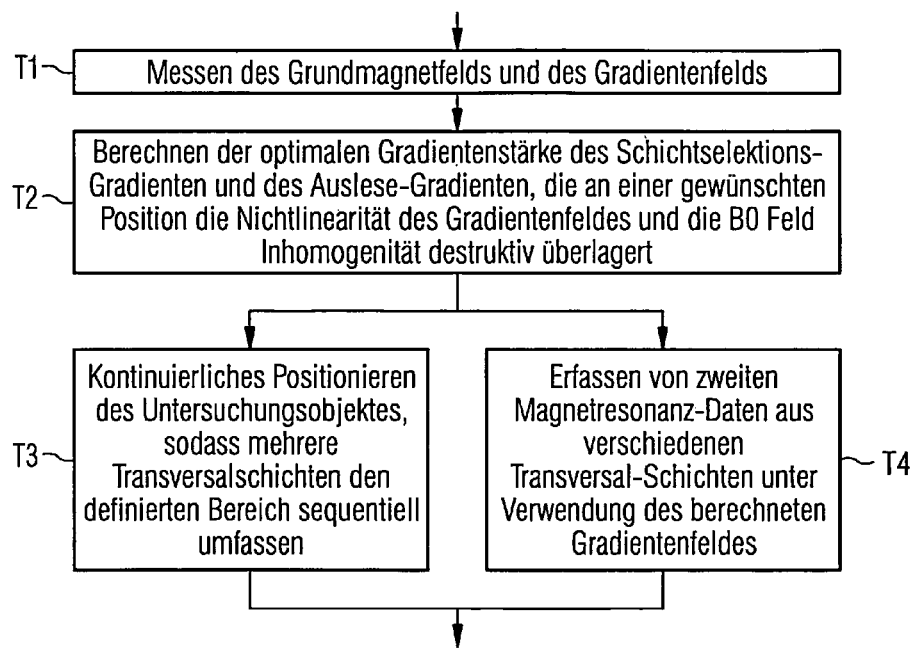
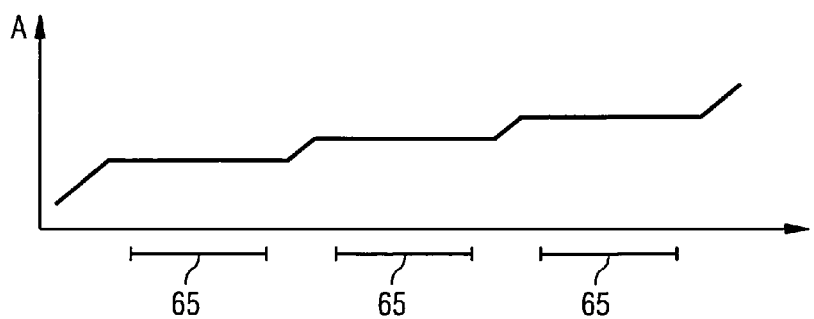

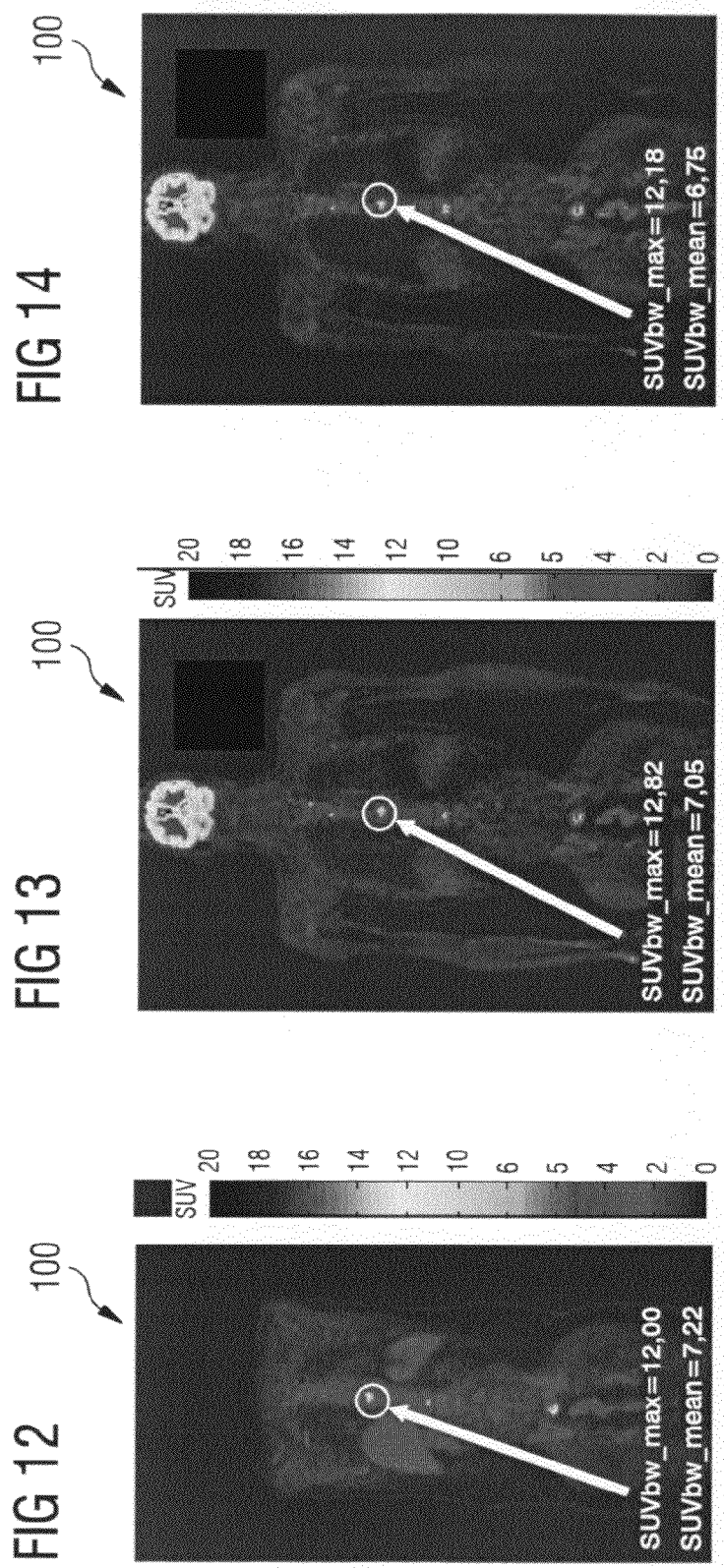

METHOD FOR CALCULATING A VALUE OF AN ABSORPTION PARAMETER IN POSITRON EMISSION TOMOGRAPHY

PRIORITY STATEMENT

The present application hereby claims priority under 35 U.S.C. §119 to German patent application number DE 10 2012 201 412.8 filed Feb. 1, 2012, the entire contents of which are hereby incorporated herein by reference.

FIELD

At least one embodiment of the present invention generally relates to a method for calculating a spatially resolved value of an absorption parameter for a positron emission tomography scan of an examination object by way of magnetic resonance tomography and/or to a magnetic resonance system and/or to a method for positron emission tomography and/or to a positron emission tomograph.

BACKGROUND

Positron emission tomography (PET) is a widely established functional imaging method. In the course of an examination, a short-lived radioactive substance is administered to an examination object or a human examination subject and its distribution in the organism is made visible by way of PET. This enables biochemical and physiological functions of the organism to be imaged. Examples of radiopharmaceuticals used for this are molecules that have been marked with a radionuclide tracer which emits positrons.

The high-energy photons resulting during the annihilation of the positron with an electron in the body of the examination subject and emitted at an angle of 180° to one another are registered by way of a plurality of detectors arranged in an annular array around the examination subject. Owing to certain physical processes e.g. preferably photons having an original energy of 511×10³ electron-volts can be used for PET. Only coincident events which are recorded by way of two oppositely disposed detectors are tracked. These events can be assigned to the photons emitted at an angle of 180° to one another.

The spatial distribution of the radiopharmaceutical in the examination region is derived from the registered, coincident decay events and a series of sectional images (slices) is computed. A spatial resolution of PET data is typically lower than the spatial resolution of other imaging methods such as e.g. computed tomography (CT) or magnetic resonance tomography (MRT).

As they pass through matter the photons produced during the annihilation are absorbed, the absorption probability being dependent on the path length through the matter and the corresponding absorption parameter $\mu$. The absorption in the tissue is described by way of an attenuation correction factor ACF. The attenuation correction factor ACF is given by $$ACF = EXP(-INT(\mu(r)dr)),$$

where EXP designates the exponential function and INT dr denotes a line integral over the path r traveled by the photon from the origin to the detector. To express it in another way, the absorption parameter $\mu$ is therefore a measure for the probability of an absorption of a photon within a volume element. The absorption probability can be quantitatively calculated from the value of the absorption parameter $\mu$.

For example, when a quantitative analysis of the PET data is to be carried out in order, say, to obtain a quantification of accumulations of the marked substance in regions of the examination subject, or when PET imaging at a particularly high resolution is to be realized, it may be worthwhile subjecting the PET data to an attenuation correction using the attenuation correction factor ACF. If the attenuation correction is carried out, uncertainties in the determination can have a great influence on the accuracy of the attenuation-corrected PET data. If e.g. the absorption parameter $\mu$ is determined only with a specific uncertainty, i.e. there is a significant error in the value of the absorption parameter $\mu$, then the attenuation correction factor ACF may also exhibit an uncertainty due to the fact that the attenuation correction factor ACF is exponentially dependent on the absorption parameter $\mu$.

In order to achieve a maximally accurate correction of the PET data which also takes higher-order, e.g. second-order, effects into account (such as, for instance, PET scattering, referred to as "scatter correction"), a distortion-free attenuation correction map (so-called "$\mu$ map"), i.e. a parameter map of the value of the absorption parameter $\mu$, may be required. In addition, so-called "scatter scaling" may necessitate a precise specification of the outline of the object. This is because the correction of the attenuation of the radiation by way of a parameter map of the value of the absorption parameter $\mu$ requires knowledge of the position of the attenuating structures and objects.

Various methods of generating such a parameter map are known. It is possible for example to determine the parameter map by way of a combined PET/CT system or a combined PET/MRT system. In the case of a PET/MRT system, a PET system and a magnetic resonance (MR) system may be present integrated in one appliance. For example, it is possible in the case of a determination of the parameter map on the basis of MR data to differentiate experimentally by way of suitable MR recording techniques between e.g. fat, water, lung and background and to assign different values of the absorption parameter $\mu$ to the different regions. Corresponding methods are known for CT data.

However, the field of view or measurable volume of MR data is restricted in all three spatial directions due to physical and technical limitations of the magnetic field homogeneity and the linearity of gradient fields. Typically, the basic magnetic field of an MR system is generated by way of a superconducting tube-shaped coil magnet. The patient or examination object is located in the tube inside the magnet. Strong spatial distortions in the MR data occur close to the edge of the tube, i.e. outside the field of view of the MR system. Particularly strong distortions cannot fulfill e.g. high specification requirements in terms of the location fidelity of an MR image or can do so only to a limited extent. The field of view of the MR system is typically specified based on such requirements.

Imaging that is true to the original outside the field of view then cannot be achieved, or can be achieved only to a limited extent, using conventional MR recording techniques. However, since objects that are important for the determination of the parameter map of the following PET measurement, e.g. the arms of a patient, can also be located at these regions outside of the examination object, it may be necessary to determine the parameter map there also. See in this regard: G. Delso et al. "The effect of limited MR field of view in MR/PET attenuation correction" in Med. Phys. 37 (2010) 2804-2812.

It is possible for example to simulate those sections of the parameter map that lie outside the normal field of view of the MR system subsequently from the PET data itself. See in this regard: J. Nuyts et al. "Completion of a Truncated Attenuation Image from the Attenuated PET Emission Data" in IEEE Nucl. Sci. Symp. Conf. Record 2010. However, such a method is generally mathematically complex and time-intensive and requires high computing capacities.

Moreover, such techniques can be subject to restrictions in respect of the PET radiopharmaceuticals which can be used, since many substances, such as rubidium for instance, accumulate only to a limited extent in peripheral regions of an examination subject, e.g. the arms. There may also be restrictions in terms of the resolvable time dynamics, since the accumulation of the radiopharmaceutical itself can follow complicated dynamics. Since in addition the PET data to be corrected itself is drawn upon as a basis for calculating the correction parameter, systematic errors can occur or intrinsic uncertainties can be present.

SUMMARY

At least one embodiment of the present invention provides improved techniques for calculating the spatially resolved value of the absorption parameter, i.e. of a parameter map, for a PET scan of an examination object using an MR system. A further embodiment of the invention is directed to a parameter map that includes the value of the absorption parameter in spatially resolved form within a first region within the field of view of the MR system and within a second region bordering on the first region and lying at the edge of the field of view.

The dependent claims define embodiment variants.

According to one embodiment, a method is provided for calculating a spatially resolved value of an absorption parameter for a positron emission tomography (PET) scan of an examination object by way of magnetic resonance tomography (MRT). The method comprises acquiring first magnetic resonance (MR) data within a first region, the first region lying within a field of view of a magnetic resonance system. The method also comprises the spatially resolved calculation of a first value of the absorption parameter from the first MR data within the first region in order to obtain a three-dimensional (3D) parameter map, such that within the first region the parameter map has the first value of the absorption parameter in spatially resolved form.

In addition, the method comprises acquiring second MR data within a second region, the second region bordering on the first region and lying at the edge of the field of view, and the spatially resolved calculation of a second value of the absorption parameter from the second MR data within the second region. The method further comprises extending the 3D parameter map by the second value of the absorption parameter calculated from the second MR data, such that within the first region and the second region the parameter map has the value of the absorption parameter in spatially resolved form.

BRIEF DESCRIPTION OF THE DRAWINGS

The above-described characteristics, features and effects of the present invention, as well as the manner in which these are realized, will become clearer and more easily understandable in connection with the following description of the exemplary embodiments, which are explained in more detail with reference to the drawings, in which:

FIGS. 3, 3A and 3B are flowcharts of a method according to one embodiment variant.

FIG. 4 is a schematic perspective view of a tube of a magnetic resonance system.

FIG. 5 is a flowchart according to another embodiment variant.

FIG. 6 illustrates a recording sequence for acquiring second MR data.

FIG. 12 shows a PET image which has been attenuation-corrected by data obtained from a CT measurement.

FIG. 13 shows a PET image in which the attenuation correction has been performed on the basis of data simulated from the PET data itself.

FIG. 14 shows a PET image which the attenuation correction has been performed by a method according to the invention.

DETAILED DESCRIPTION OF THE EXAMPLE EMBODIMENTS

Figure 1:
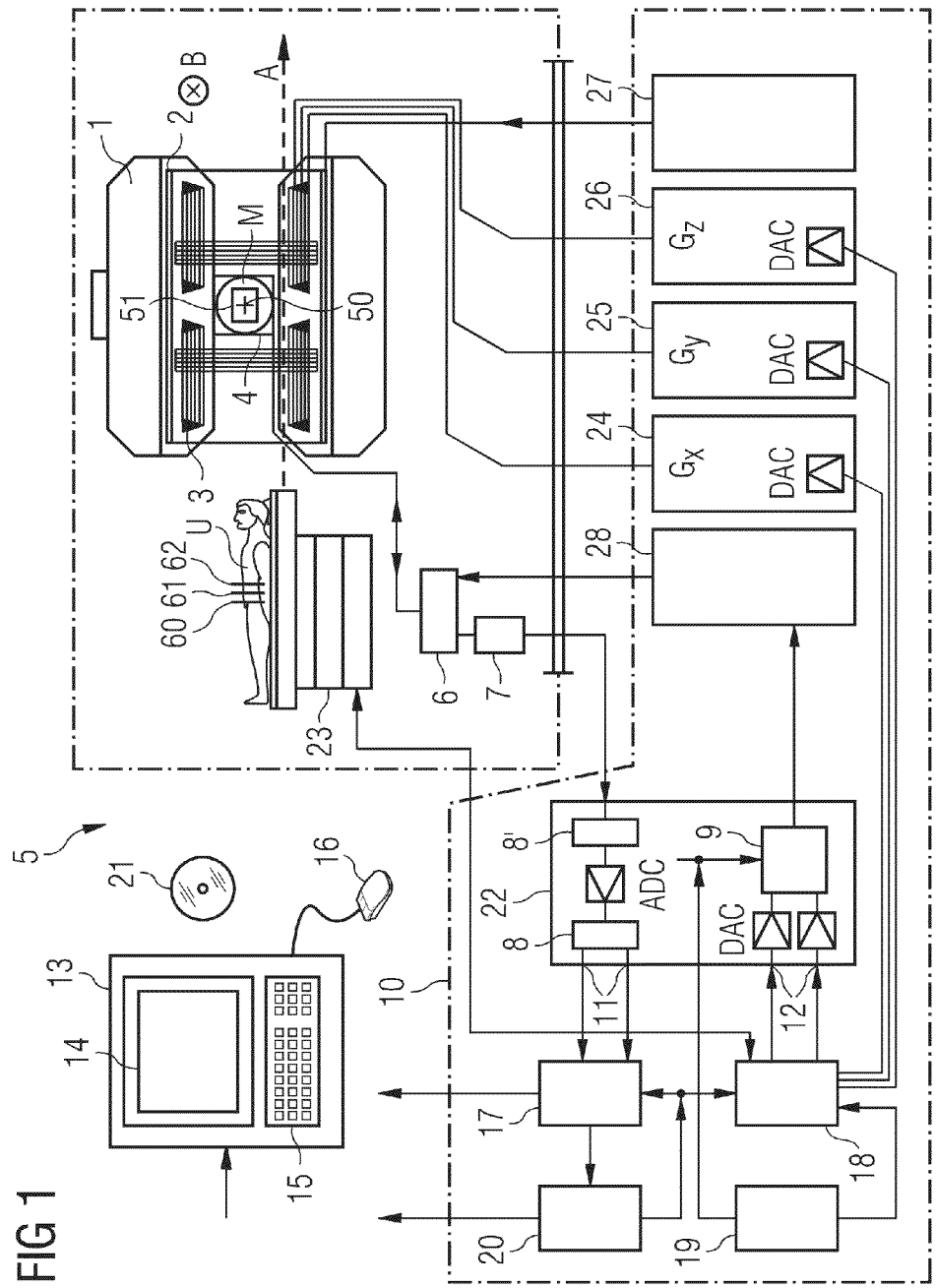
FIG. 1 is a schematic view of a magnetic resonance system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/ or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

According to one embodiment, a method is provided for calculating a spatially resolved value of an absorption parameter for a positron emission tomography (PET) scan of an examination object by way of magnetic resonance tomography (MRT). The method comprises acquiring first magnetic resonance (MR) data within a first region, the first region lying within a field of view of a magnetic resonance system. The method also comprises the spatially resolved calculation of a first value of the absorption parameter from the first MR data within the first region in order to obtain a three-dimensional (3D) parameter map, such that within the first region the parameter map has the first value of the absorption parameter in spatially resolved form.

In addition, the method comprises acquiring second MR data within a second region, the second region bordering on the first region and lying at the edge of the field of view, and the spatially resolved calculation of a second value of the absorption parameter from the second MR data within the second region. The method further comprises extending the 3D parameter map by the second value of the absorption parameter calculated from the second MR data, such that within the first region and the second region the parameter map has the value of the absorption parameter in spatially resolved form.

By way of such a method, it may be possible firstly to determine the parameter map for a region within the field of view of the MR system and then, on the basis thereof, extend the parameter map.

It may be possible for example to acquire the first MR data by way of a Dixon MR recording technique in which the phase angle of the magnetization in fat and water at an echo time instant is used in order to distinguish between fat and water fractions in the examination object. It may be possible for example to differentiate between fatty tissue, water, lung and background by way of such a Dixon MR recording technique. For these different types it may then be possible to calculate a corresponding value of the absorption parameter in each case and store it in spatially resolved form in the parameter map. Calculate in such a case can mean that the different types of matter, in other words fatty tissue, water, lung and background, are assigned different first values of the absorption parameter.

Also known are MR recording techniques which permit imaging that is true to the location, i.e. imaging with minor spatial distortions, of examination objects in a region lying outside the conventionally usable field of view of the MR system, in other words e.g. in a peripheral area of the tube. Since such MR recording techniques typically suffer from certain restrictions due to physical and technical limitations, a direct combination of this data with MR data acquired e.g. by way of a Dixon recording technique for the purpose of determining the parameter map in a region within the field of view of the MR system can be problematic.

In this case the parameter map or "μ map" can be for example a 3D matrix which assigns specific values of the absorption parameter to specific location points within the examination object. The locations within the examination object at which only a background signal is measured, e.g. because air is present there, can then be assigned a different value of the absorption parameter from those locations at which e.g. fat or water is present. For example, the value of the absorption parameter for air is very low (less than 0.0001 l/cm) according to the ratio of the density of air to the density of human tissue (approx. 1:1000). Soft tissue of an examination object has for example a value of the absorption parameter in the order of 0.1 l/cm, and bone has a value of the absorption parameter of 0.17 l/cm.

A high degree of precision in the spatial determination of the value of the absorption parameter can typically be achieved by way of a corresponding MR recording technique. Within the first region it is then possible to provide the parameter map in such a way that it has the first value of the absorption parameter in spatially resolved form.

Calculating the value of the absorption parameter from the MR data can in this case include e.g. performing mathematical computing operations based on the MR data or reading out the values from a table with the aid of predefined assignment functions or a threshold value comparison or similar. In this context the calculation is not to be interpreted narrowly as a step necessarily comprising mathematical operations.

In one embodiment variant, the calculation of the value of the absorption parameter may include segmenting the MR data into tissue types and assigning the thus segmented MR data to values of the absorption parameter. That is to say, it may not be possible e.g. to calculate the absorption parameter directly from the MR data because this does not permit the electron density to be deduced directly. However, keeping available specific absorption parameter values with an assignment to the thus segmented tissue types can nonetheless permit an accurate determination of the parameter map.

It is for example possible that the first MR data within the second region exhibits greater spatial distortions than the second MR data. Then it may happen that it will also not be possible to determine by way of the first MR data the value of the absorption parameter within the second region with a precision that is required for an attenuation correction of PET data. In other words there may be a great error in the first value of the absorption parameter within the second region. The cause of this may be e.g. that conventional Dixon recording techniques exhibit a great spatial distortion within the second region, since there e.g. a basic magnetic field of the MR system which is used for aligning the magnetization has inhomogeneities and/or gradient fields for spatial encoding of the MR data have nonlinearities.

For example, the spatial distortion of the first MR data can exceed a threshold value at the boundary between the first region and the second region. The threshold value can be chosen such that if the MR data has a spatial distortion within the threshold value the precision with which an attenuation correction can be performed will be sufficient for the respective task.

In this regard, the second MR data can be recorded by way of an MR recording sequence which includes the generation of a gradient field with a nonlinearity of its spatial dependence in such a way that in the second region the nonlinearity compensates for a spatial inhomogeneity of a basic magnetic field. Typically, as explained hereinabove, nonlinearities of the gradient fields and inhomogeneities of the basic magnetic field of the MR system are the cause of spatial distortions of the MR data in peripheral areas, e.g. the tube of the MR system, i.e. outside the field of view. If the MR recording sequence for acquiring the second MR data is embodied in such a way that the nonlinearities of the gradient field are compensated specifically with the inhomogeneities of the basic magnetic field, then it may be possible to achieve a reduction in the spatial distortion of the second MR data or to keep the distortion below a tolerable threshold value. It may then be possible to calculate the second value of the absorption parameter with a reduced error on the basis of the second MR data.

On that basis, it may be possible to extend the parameter map so that it provides the values of the absorption parameter within the first and second region e.g. of a following attenuation correction. However, the degrees of freedom in execution in the MR recording sequence for acquiring the second MR data may be limited due to physical and technical limitations in the peripheral area of the field of view of the MR system. For example, under certain conditions it may not be possible to perform a Dixon MR recording technique in the second region.

It may also be possible for the first MR data to have a higher spatial resolution than the second MR data. In particular it may be possible e.g. for the spatial resolution of the first MR data in the layer selection direction, i.e. in the axial direction along the tube of the MR system and parallel to the basic magnetic field, to have a lower spatial resolution than the second MR data. Thus, the spatial resolution of the MR data can be critical for the spatial resolution with which the value of the absorption parameter can be determined. However, a maximally high spatial resolution of the value of the absorption parameter and consequently of the parameter map may permit a high level of precision in the attenuation correction.

Accordingly, at least one embodiment of the method can further comprise: Interpolating the second value of the absorption parameter calculated from the second MR data onto the spatial resolution of the first value of the absorption parameter. It may be possible for example, by use of linear interpolation between two spatially adjacent data points of the second value, also to obtain approximated second values for locations which are situated between the locations with actually measured second values. By this, it may be possible to align the spatial resolutions.

In this case the interpolation within the second region can take into account in particular outlines of the examination object. This can have e.g. the effect that a linear interpolation can be avoided between data points of the absorption parameter value which lie inside and outside the examination object, i.e. which are arranged specifically in the peripheral area of the examination object. If, namely, a linear interpolation is made between such data points, the thus obtained approximated data points can have higher uncertainties than if e.g. with knowledge of the outline of the examination object a stepped transition, say, is used instead of linear interpolation. Such a stepped transition can match the actual conditions better than a gradual transition since, as explained hereinabove, values of the absorption parameter for air differ greatly from values of the absorption parameter for human tissue.

It is also possible that the interpolation additionally includes the spatially resolved weighting of the second value of the absorption parameter calculated from the second MR data with a quality factor, the quality factor quantifying a spatial distortion of the associated second MR data and the interpolation taking greater account of second values of the absorption parameter having a higher quality factor. This is because it may be possible that the second MR data within the second region also exhibits a significant uncertainty e.g. in the location, i.e. spatial distortions or other signal noise. However, this uncertainty can vary as a function of the location within the second MR data. Thus, if parts of the second MR data are affected by a smaller spatial distortion than other parts, the interpolation can take greater account of those second values of the absorption parameter which have been calculated from second MR data having precisely a lower spatial distortion.

The method can furthermore include the determination of the position and the outline of the examination object imaged by way of the second MR data, wherein the second value of the absorption parameter is calculated based on the determined position and the outline. The calculation can be performed e.g. manually or automatically or in a semi-automated manner.

For example, it may be possible for the calculation for regions of the examination object lying within the determined outline to include the assignment of a determined second value of the absorption parameter and for regions lying outside the determined outline to include the assignment of a further determined second value of the absorption parameter. The determined second value of the absorption parameter can be e.g. an average value of the actual absorption parameter value that is characteristic of this region of the examination object. If namely e.g. arms of an examination subject are arranged within the second region, then it can be known that the value of the absorption value of the arms averages e.g. 0.1 to 0.2 l/cm. The further determined second value of the absorption parameter which is assigned to the regions outside the outlines, i.e. outside the examination object, can be different from the determined second value and be chosen e.g. equal to an absorption parameter value for air.

The method can furthermore include the acquisition of the second MR data (81) also within the first region ($\mu$) and the segmentation of the second MR data into second MR data which images the first and the second region in each case, and the discarding of the second MR data which images the first region. It may namely be that the MR recording sequence used to acquire the second MR data also generates MR data within the first region. Then it can be worthwhile to discard that MR data which relates to the first region. A parameter map can namely be generated in the first region on the basis of the first MR data, e.g. by way of a Dixon MR recording technique. Typically, the thus calculated first value of the absorption parameter can have a lesser uncertainty than the second value of the absorption parameter within the first region. For this reason it may be desirable to discard the second MR data within the first region and consequently not use the data for calculating an absorption parameter value.

It may e.g. be possible for the first MR data and the second MR data to be recorded, not concurrently, but consecutively, i.e. with an offset in time. It may then be necessary, in order to discard the second MR data which images the first region, to determine the position of the first region within the first and the second MR data as accurately as possible, e.g. on the basis of the MR data itself. In other words it may be worthwhile to synchronize the structures imaged by use of the first and second MR data in order to discard the second MR data in a targeted manner and e.g. minimize motion artifacts. This can include e.g. registering MR images based on the first and the second MR data in order to identify structures. Starting from this basis, the first region can then be localized both in the first and in the second MR data and the boundary of the regions found precisely in the MR data.

According to a further aspect, at least one embodiment of the present invention relates to a method for positron emission tomography, comprising the acquisition of PET data and the correction of the PET data by way of an attenuation correction parameter. In this case the attenuation correction parameter is obtained from a parameter map of a value of an absorption parameter which is obtained by way of a method according to a further aspect of at least one embodiment of the invention. If the attenuation correction parameter is calculated from a parameter map which has the value of the absorption parameter in spatially resolved form both within a first region and within a second region bordering on the first region at the edge of the field of view of an MR system, then a high degree of precision can be achieved in the attenuation correction for the PET data. In particular, the attenuation correction can also be extended to such parts of an examination object which lie at the edge of a field of view of the MR system. Typically, this is where arms of an examination subject may be located.

According to a further aspect, at least one embodiment of the invention relates to a magnetic resonance system which comprises a recording device for recording MR data of an examination object arranged in a tube of the MR system, the recording device being configured to perform at least: acquisition of first MR data within a first region, the first region lying within a field of view of the MR system, and acquisition of second MR data within a second region, the second region bordering on the first region and lying at the edge of the field of view.

The magnetic resonance system of at least one embodiment further comprises a processor with attached memory which is configured to perform at least: spatially resolved calculation of a first value of the absorption parameter from the first MR data within the first region in order to obtain a three-dimensional parameter map such that within the first region the parameter map has the first value of the absorption parameter in spatially resolved form, and spatially resolved calculation of a second value of the absorption parameter from the second MR data within the second region and extension of the 3D parameter map by the second value of the absorption parameter calculated from the second MR data such that within the first region and the second region the parameter map has the value of the absorption parameter in spatially resolved form.

For example, the arms of an examination subject can be arranged within the second region. Then it can be possible for the parameter map of the absorption parameter value also to include those regions at the edge of the field of view of the MR system in which the arms are arranged. The precision with which an attenuation correction parameter can be calculated in a PET measurement can be increased in this way.

In particular e.g. the first region can extend in the radial direction inside a first radius in relation to a central axis of the tube of the MR system and the second region can extend in the radial direction between the first radius and a second radius in relation to the central axis, where the second radius is greater than the first radius. The basic magnetic field of the MR system can be aligned e.g. along the central axis, i.e. in the axial direction. For example, the tube of the MR system can have a radius of 30 cm, though the conventional measurement range, i.e. the field of view, only has a radius of e.g. 25 cm. With conventional MR recording sequences, strong spatial distortions can occur in the region outside the field of view and within the tube due to inhomogeneities in the basic magnetic field and/or nonlinearities of the gradient field. In other words, the first radius can be e.g. 25 cm and the second radius just under 30 cm.

Since it may be that the inhomogeneities of the basic magnetic field and/or the nonlinearities of the gradient field are dependent on the axial position, the axial extent of the second region may be limited. Only within a second region that is limited in the axial direction may it namely be possible to compensate for a specific inhomogeneity with a specific nonlinearity and in this way to obtain second MR data having less spatial distortion.

Effects can be achieved for such a magnetic resonance system which correspond to those effects which can be achieved by way of a method according to an aforesaid aspect of an embodiment of the invention.

According to a further aspect, at least one embodiment of the invention relates to a positron emission tomograph which comprises a recording device which is configured for acquiring PET data. The positron emission tomograph additionally comprises a processor which is configured for correcting the PET data by way of an attenuation correction parameter, the attenuation correction parameter being obtained from a parameter map of a value of an absorption parameter, which map is obtained by way of a method according to an aforesaid aspect. Effects can be achieved for such a positron emission tomograph which correspond to those effects which can be achieved for a method according to an aforesaid aspect of at least one embodiment of the invention.

The above-disclosed features can be used without leaving the scope of protection of the present invention not only in the corresponding explicitly described combination, but also in other combinations or in isolation.

FIG. 1 shows a schematic view of an MR system 5. Here, a magnet 1 generates a temporally constant strong basic magnetic field for aligning nuclear spins in an examination region of an examination object U, e.g. a human examination subject. For example, the basic magnetic field can be aligned along the direction designated by A in FIG. 1, i.e. along the axial direction of the tube of the MR system 5. The examination object U in the case of FIG. 1 is an examination subject who is positioned on a table 23. The table 23 can be introduced into the tube of the magnetic resonance system 5 along the direction designated by A and positioned in a targeted manner along the direction.

The basic magnetic field is generated e.g. by the basic field magnet 1 by way of superconducting coils. In FIG. 1, the largest component of the basic magnetic field points along the direction A, wherein deviations e.g. in strength or also direction can also occur in peripheral regions of the tube of the MR system 5. The high homogeneity of the basic magnetic field that is necessary for the MR measurement is given in a typically spherical measurement volume M into which the parts of the examination object U that are to be examined are introduced, e.g. through positioning of the table 23. For example, the measurement volume M can contain an isocenter 50 of the MR system 5. The isocenter 50 can lie on the central coil axis of the magnet 1, i.e. at or close to the center point of the tube. The measurement volume M is arranged within the field of view of the MR system 5 because there the different measurement parameters lie within a tolerance range.

Shim plates made of ferromagnetic material are mounted at a suitable point in order to support the homogeneity requirements and in particular to reduce or suppress time-invariable influences. Time-variable interference effects are reduced by way of the shim coils 2 and a suitable controller 27 for the shim coils 2.

A cylinder-shaped gradient coil system 3 including e.g. three part-windings is inserted into the basic field magnet 1. Each part-winding is supplied with current by a corresponding amplifier 24 to 26 for generating a linear gradient field in the respective direction of a Cartesian coordinate system. The amplifiers 24 to 26 each comprise a digital/analog converter which is driven by a sequence controller 18 for accurately timed generation of gradient pulses.

Located within the gradient field system 3 is a radio-frequency antenna 4 that converts the radio-frequency pulses emitted by a radio-frequency power amplifier into an alternating magnetic field in order to excite a precession of the nuclear spins of the examination object U. The radio-frequency (RF) antenna 4 includes one or more RF transmit coils and a plurality of RF receive coils in the form of a, for example, annular, linear or matrix-shaped array of coils.

The alternating field emanating from the precessing nuclear spins, i.e. usually the nuclear spin echo signals caused by a pulse sequence made up of one or more radio-frequency pulses and one or more gradient pulses, is converted e.g. inductively into a voltage by the RF receive coils of the radio-frequency antenna 4. The voltage can be recorded as a measurement signal. The voltage is supplied to a radio-frequency receive channel 8, 8' of a radio-frequency system 22 by way of an amplifier 7.

The radio-frequency system 22 additionally has a transmit channel 9 in which the radio-frequency pulses for exciting the nuclear magnetic resonance are generated. In the process the respective radio-frequency pulses are represented in the sequence controller 18 e.g. digitally as a series of complex numbers based on a pulse sequence predefined by the system computer 20. This numeric sequence is supplied as a real and an imaginary part by way of an input 12 in each case to a digital/analog converter in the radio-frequency system 22, and from the latter to the transmit channel 9. In the transmit channel 9, the pulse sequences are modulated onto a radio-frequency carrier signal whose fundamental frequency corresponds to the resonant frequency of the nuclear spins in the measurement volume M. The modulated pulse sequences are supplied to the RF transmit coil of the radio-frequency antenna 4 by way of an amplifier 28. The combination of pulse sequences and activation of the gradient field is referred to as a recording sequence.

A transmit/receive duplexer 6 permits operation to be switched between transmitting and receiving mode. The RF transmit coil of the radio-frequency antenna 4 radiates the radio-frequency pulses for exciting the nuclear spins into the measurement volume M and samples resulting echo signals by way of the RF receive coil. The time base for the radio-frequency system 22 and the sequence controller 18 is made available to a synthesizer 19.

The acquired measurement data can be used by an image processor 17 to reconstruct an MR image as a graphical representation of the MR data. A system computer or a processor 20 handles the administration of the measurement data, the image data and the control programs, as well as further processing of the MR data. Typically, the processor 20 also comprises a memory. Corresponding control programs for generating an MR image which are stored e.g. on a DVD 21 or a corresponding data medium are selected, and the generated MR image is displayed, by way of a terminal 13 which comprises a keyboard 15, a mouse 16 and a monitor 14.

However, it is not always necessary to display an MR image in actuality, e.g. when the system computer or the processor 20, instead of generating an MR image, subjects the generated MR data to some other form of further processing. For example, it may be possible for the processor 20 to calculate from the MR data spatially resolved values of an absorption parameter $\mu$ which are able to be combined in a 3D parameter map. The values can be calculated by processor 20 on the basis of specific computational rules. For example, the MR data can obtain indications as to which type of material, e.g. fatty tissue, water, lung or background, is present at a specific location. Based on this information which processor 20 receives or calculates from the MR data, processor 20 can assign different values of the absorption parameter $\mu$ to the different location points.

For example, the link between the different types of material and specific values of the absorption parameter $\mu$ can be stored in advance by way of terminal 13 and then retrieved automatically. It is also possible for system computer 20 to establish the outlines of the examination object U in the MR data, e.g. automatically by way of image registration or manually by way of user input. Once the outlines have been established, system computer 20 can assign a determined value of the absorption parameter to those spatial regions of the examination object U that lie within the determined outlines, and a further determined value of the absorption parameter to regions lying outside of the determined outlines, i.e. outside the examination object. For example, the absorption parameter value for air can namely be substantially lower than the absorption parameter value within the outlines of the examination object, i.e. for tissue, etc.

A parameter map of the absorption parameter value provided by system computer 20 can be used for attenuation correction of PET data. For example, the MR system 5 can be a combined MR/PET system 5 (not depicted in FIG. 1). It may then be possible also to record PET data of the examination object U, e.g. without the need to represent the examination subject. The PET data can then be attenuation-corrected directly by way of the parameter map from processor 20. It is, however, also possible for the parameter map provided by processor 20 to be exported and used for a separate PET measurement. PET systems are well-known to the person skilled in the art, so there is no need for any further explanation thereof at this juncture.

It may be possible in particular for processor 20 to apply different techniques for calculating the value of the absorption parameter $\mu$ for different MR data originating e.g. from different regions of the examination object U or different regions within the tube of the MR system 5. The measurement volume M is namely e.g. spatially delimited by the basic magnetic field homogeneity and the linearity of the gradient field. Measurements outside the field of view, in other words in regions in which the basic magnetic field exhibits inhomogeneities and the gradient field exhibits nonlinearities which are e.g. greater than a threshold value, can lead to strong spatial distortions in the images based on MR data. In other words, regions of the examination object U which are disposed outside the measurement volume M do not appear in the MR images at the point at which they are located in reality. The exact size of the measurement volume M within the MR system 5, in particular the dimensions in the radial direction, is dependent on many parameters, such as design format and type of the basic field magnet, voltage supply, obstructions in the region of the patient couch, etc. However, the applicability of the technical teachings, as presented here, is not limited by the actual dimensions.

In a conventional magnetic resonance system 5 having for example a tube diameter of 60 cm, the measurement volume M can have a diameter with a value within the range from 45 cm to 55 cm or 48 cm to 52 cm, particularly frequently approximately 50 cm. This means that spatial distortions will occur to an increased extent in a peripheral region of approximately 5 cm to 15 cm, or 8 cm to 12 cm, particularly frequently of approx. 5 cm-along the inner circumference of the tube of the MR system 5.

Typically, the arms of the examination subject U are located in this region. In order e.g. to enable the arms of the examination subject U also to be taken into account for the attenuation correction of PET data, system computer 20 must be embodied in such a way that it provides the parameter map of the value of the absorption parameter $\mu$ not only within the measurement region M, but also in the regions adjacent thereto in which the arms of the examination subject U are located. The region 51, which borders on the measurement region M, and consequently on the field of view of the magnetic resonance system 5, shall be referred to hereinbelow as the second region 51.

Figure 2:
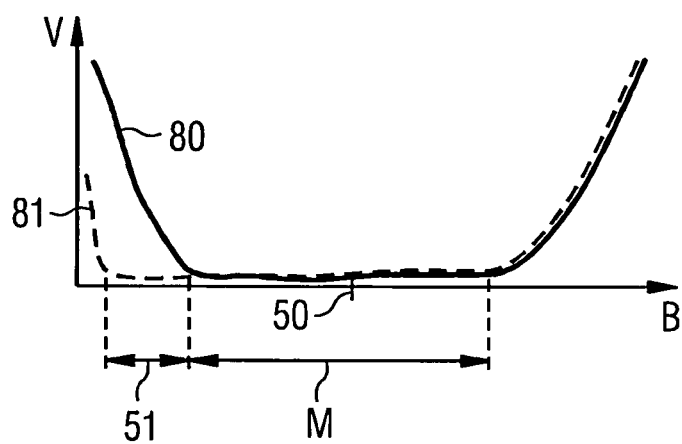
FIG. 2 illustrates the measurement range (field of view) of a magnetic resonance system in relation to a first and second region.

For example, FIG. 2 shows a possible dependence of the spatial distortion V on a position along the direction designated by B in FIG. 1, i.e. a radial direction in relation to the tube of the magnetic resonance system 5. The continuous line in FIG. 2 describes the distortion V of conventionally recorded first MR data 80. The MR data 80 may for example have been recorded by way of a Dixon recording technique in which the phase angle of the magnetization in fat and water at an echo time instant is used in order to differentiate between fat and water fractions in the examination object U of FIG. 1. This information can then be used to determine the absorption parameter value by way of the system computer 20. As is also evident from FIG. 2, the first MR data 80 exhibits strong distortions V in a peripheral region. At radial distances to the isocenter 50 which exceed a specific value, e.g. 25 cm in the case of conventional MR systems, the distortion V assumes such extreme values that the first MR data 80 is affected by a significant error. With conventional techniques, such first MR data 80 cannot be used to determine a meaningful value of the absorption parameter μ.

However, methods are known which enable MR data having a lesser distortion V to be generated in the second region 51 adjacently joining the measurement region M in the radial direction. The second MR data 81 is represented by a dashed line in FIG. 2. The second MR data 81 can be generated for example by way of an MR recording sequence which compensates for spatial inhomogeneities of the basic magnetic field by way of spatial nonlinearities of the gradient field in such a way that the second MR data 81 in particular no longer exhibits any distortions V. Such methods are well-known to the person skilled in that art, so there is no need to deal with them in any further detail here.

The MR recording sequences for acquiring the first MR data 80 and the second MR data 81 may, however, differ from one another significantly, e.g. in terms of the region covered, the spatial resolution, the information content, etc., with the result that no direct combination of the MR data 80, 81 or of the value of the absorption parameter μ calculated on the basis thereof is possible.

Referring to FIG. 3, a method will be explained below which not only enables the value of the absorption parameter μ to be calculated in spatially resolved form using the first and second MR data 80, 81 for subsequent PET, but also allows PET data based thereon to be attenuation-corrected. The method starts with step S1.

Firstly, in step S2, the first MR data 80 is acquired within the first region M with the aid of a Dixon recording technique. The first MR data 80 can have a first spatial resolution. The first region M can also have a certain extension along the axial direction of the tube of the MR system 5 designated by A in FIG. 1, i.e. in the layer selection direction. On that basis, in step S3, a first value of the absorption parameter μ within the first region M can be calculated from the first MR data 80. Methods for this purpose which e.g. establish an association between the different types of matter obtained from a Dixon MR recording technique (tissue, water, air, lung) and absorption parameter values are well-known to the person skilled in the art. The first value of the absorption parameter μ calculated in spatially resolved form can then be stored in a parameter map in step S4. The parameter map can be in the form of a matrix and thus assign a value of the absorption parameter μ to the different location points.

In step S5, the second MR data 81 is acquired within the first and the second region M, 51. For this purpose use is made of an MR recording technique as described in the foregoing with reference to FIG. 2. Such a recording technique permits the second MR data 81 to have a low distortion V in the second region 51 also. This can be accomplished for example by way of an MR recording sequence which compensates for spatial inhomogeneities of the basic magnetic field of the MR system 5 by way of spatial nonlinearities of the gradient field. However, the second MR data 81 typically has a lower depth of information in terms of the material at a location, with the result that the absorption parameter value cannot be determined in the same way as happened for the first MR data in step S3.

In step S6, a segmentation of the second MR data 81 is performed initially, i.e. those parts of the second MR data 81 are identified which originate from the first region M and the second region 51. Because steps S2 and S5 can take place offset in time and the MR data 80, 81 can have different spatial resolutions, etc., step S6 can include e.g. an image registration or employ similar methods which permit the edge of the regions M, 51 to be found in the second MR data 81. In step S7, the second MR data 81 belonging to the first region is then discarded. This can be desirable since a calculation of the absorption parameter value for the first region M has already taken place on the basis of the first MR data 80 and consequently the second MR data 81 is no longer required in this region M.

In step S8, the outlines and the position of the examination object U in the second MR data 81, which now relates to the second region 51, are then determined. This step too can include e.g. an image registration or similar methods. On that basis, in step S9, a second value of the absorption parameter μ within the second region 51 can be calculated on the basis of the second MR data 81 (from step S5) and the determined outlines and position of the examination object U (from step S8). It is for example possible to assign a determined second value of the absorption parameter μ to those regions of the examination object U lying within the outlines, and a further determined second value of the absorption parameter μ to those regions lying outside the examination object U, i.e. disposed outside the outlines. For example, the determined second value can be different from the further determined second value and have a characteristic, e.g. averaged, value for the regions of the examination object U located in the second region, e.g. the arms of an examination subject.

In step S10, a check is carried out to determine whether the spatial resolution of the first MR data 80 is unequal to the spatial resolution of the second MR data 81. In particular the spatial resolution both of the first and of the second MR data 80, 81 can have different values in different directions, such that the check in step S10 can take place separately for the three spatial dimensions. For the sake of simplicity, reference is made in the following only to one of the three spatial dimensions. If it is established in step S10 that the spatial resolution of the first MR data 80 is equal to the spatial resolution of the second MR data 81, then the parameter map, as obtained from step S4, can be extended in step S13, and specifically by the second value of the absorption parameter μ calculated from the second MR data 81. This is because the spatial resolution of the first value and of the second value is then equal. And because the parameter map typically has a three-dimensional matrix structure, wherein different matrix entries are assigned to different locations and the spatial distance between neighboring matrix entries assumes e.g. the same values, it must be ensured in step S10 that the spatial resolution of the first MR data 80 is commensurable with the spatial resolution of the second MR data 81. In other words, the grid of the MR data points is e.g. identical in the first and in the second MR data.

If, however, it is established in step S10 that the spatial resolution of the first MR data 80 is not equal to the spatial resolution of the second MR data 81, then the method continues with step S11. There, the second value of the absorption parameter μ calculated from the second MR data 81 is initially weighted with a quality factor Q, the quality factor Q quantifying the strength of the spatial distortions in the second MR data 81. Based on the weighting, the second value of the absorption parameter μ calculated from the second MR data 81 is interpolated in step S12 taking into account the outlines and the quality factor Q. For example, those second values of the absorption parameter μ which have a higher quality factor Q, i.e. a lower strength of spatial distortion V, can be taken into account to a greater extent in the interpolation.

The type of interpolation can also depend on whether the locations belonging to the second value of the absorption parameter μ are situated only inside or outside the outlines of the examination object U or whether the interpolation is carried out between locations which are situated inside and outside the outlines. If, namely, the value is interpolated e.g. between such second values of the absorption parameter μ which are situated only within the outlines, i.e. within the examination object U, then a linear interpolation can take place, possibly taking account of the quality factor Q. If, however, an interpolation takes place between such second values of the absorption parameter μ which are in each case situated inside and outside the outlines, then e.g. a stepped interpolation can be carried out instead of a linear interpolation. The interpolation in step S12 can ensure that the spatial resolution of the first value of the absorption parameter μ calculated from the first MR data 80 is equal to the spatial resolution of the second value of the absorption parameter μ calculated from the second MR data 81, although the spatial resolution of the first and second MR data 80,81 is not equal. The parameter map can then be extended accordingly in step S13.

Position emission tomography data is acquired in step S14. In step S15, the PET data acquired in step S14 is corrected by way of the absorption parameter values from the parameter map by carrying out an attenuation correction. The attenuation correction can include the forming of a line integral via the absorption parameter along the travel path of the PET photons. The corrected PET data can then be processed further, e.g. as a PET image. The method terminates at step S16.

Individual steps of the method will be explained in more detail below with reference to FIGS. 4 to 18. Firstly, referring to FIG. 4, the geometric relationship between the first subregion M and the second subregion 51 is explained in more detail. The tube of an MR system 5 is shown in FIG. 4. The isocenter 50 is indicated as the geometric center point of the tube. The direction A runs in the axial direction of the tube, while the direction B runs in the radial direction. Three layers 60, 61, 62 of the examination subject U are also shown. The layers are also indicated graphically in FIG. 1. As can be seen from FIG. 4, the second subregion 51, in which the first MR data 80 has a high spatial distortion V, but the second MR data 81 has a low distortion V, is located offset in the radial direction B with respect to the isocenter 50 in the direction of the periphery of the tube of the first MR system 5 (though inside the tube).

The first region or the measurement region M is located between isocenter 50 and subregions 51 in the radial direction. The second region 51 has a limited extension in the axial direction A, e.g. because the inhomogeneities of the basic magnetic field can be compensated for by nonlinearities of the gradient field, e.g. of the readout gradient field or of the layer selection gradient field, only in a specific limited range along the direction A.

Referring to FIGS. 5 and 6, two embodiment variants are illustrated which show how the second MR data 81 can be recorded by way of the MR recording sequence for the different layers 60, 61, 62 of the examination object U. FIG. 5 shows a flowchart which breaks down step S5 of FIG. 3 in more detail. Firstly, in step T1, the basic magnetic field and the gradient field are measured. The measurement of these two variables can take place for example within the layer 61 close to the isocenter 50. The nonlinearities of the gradient field are determined on that basis. Next, in step T2, the optimal gradient strength of the layer selection gradient and/or of the readout gradient is calculated which destructively overlays the nonlinearity of the gradient field and the inhomogeneity of the basic magnetic field at the desired position along the axial direction A. Steps T3 and T4 are then performed in parallel.

In the process the table 23 on which the examination subject U is placed is positioned continuously, e.g. at a constant speed, in step T3 in such a way that the different transverse layers, e.g. the layers 60, 61, 62, successively comprise the second region 51 at which the optimal gradient strength was calculated in step T2. Simultaneously, second MR data 81 can then always be acquired for the corresponding layer in step T4. It should be understood that other techniques also exist in order to obtain a spatial resolution of the second MR data 81 along the axial direction A, i.e. the layer selection direction, in spite of a dependence of the nonlinearities of the gradient field or inhomogeneities of the basic magnetic field on the position along the direction A. Such techniques can, however, cause the spatial resolution along the direction A to be lower than the corresponding spatial resolution of the first MR data 80.

FIG. 6 shows such an alternative embodiment variant, which represents the execution of MR recording sequences for the purpose of acquiring second MR data 81. FIG. 6 shows the position of table 24 along the axial direction A as a function of time. As is apparent from FIG. 6, in contrast to continuous positioning, as shown with reference to FIG. 5, sequential positioning for the purpose of acquiring the second MR data 81 by way of recording sequences 65 is also possible. It can be seen from FIGS. 5 and 6 that the thus obtained second MR data 81 is limited in terms of its spatial resolution or has a lower spatial resolution than the first MR data 80.

Figure 7:
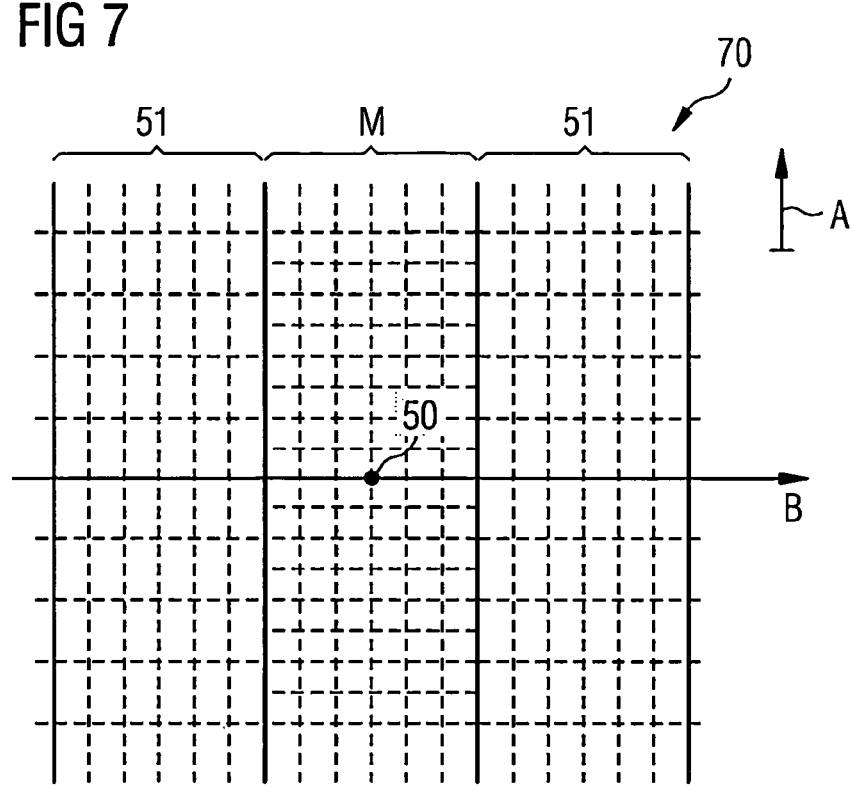
FIG. 7 illustrates a parameter map of an absorption parameter value in a first region and a second region.
Figure 8:
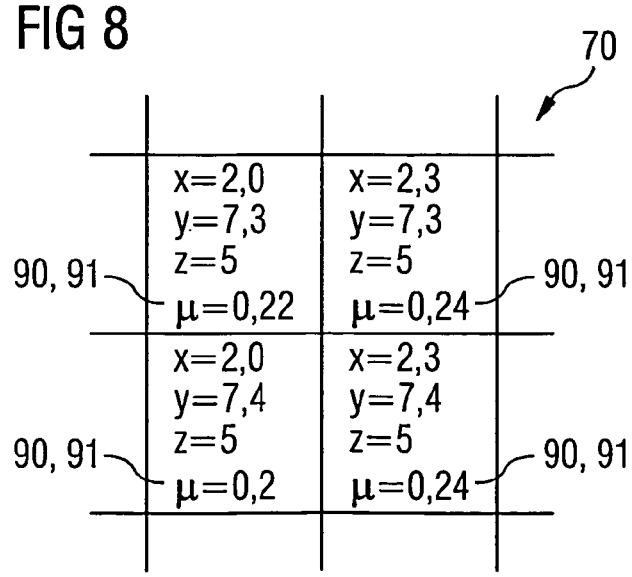
FIG. 8 illustrates the parameter map from FIG. 7 with a greater level of detail.

FIG. 7 shows a simple parameter map 70 of the absorption parameter value along a plane defined by the directions A and directions B. Areas of the parameter map 71 which correspond to the first region M and the second region 51 are indicated graphically. In direction A, the parameter map 70 has a lower spatial resolution within the second region 51 than within the first region M. In direction B, however, it has the same spatial resolution in the two regions M, 51.

Typically, the parameter map 70 has a matrix structure, wherein different elements denote different locations. This is illustrated in more detail with reference to FIG. 8. Four entries of the parameter map 70 are represented by way of example in FIG. 8. As can be seen, different entries of the parameter map 70 are assigned different locations, designated in this case by way of the coordinates x, y and z, e.g. as an offset with respect to the isocenter 50 of the MR system 5 or with respect to another reference point. Whereas in the parameter map 70 of the embodiment variant according to FIG. 8 these location points are explicitly provided and stored within the parameter map, it is e.g. also possible for the different entries of the parameter map 70 to describe a fixed grid with given distances between the different entries of the parameter map 70. The value 90, 91 of the absorption parameter μ is also stored in the parameter map 70. The value 90, 91 is stored for example in units of 1 l/cm. In this case the absorption parameter value can be the first value 90 calculated from the first MR data 80 or the second value 91 calculated from the second MR data 81.

It can be advantageous to perform an interpolation of the second value 91 of the absorption parameter μ within the second region 51 if the value has a lower spatial resolution there than the first value 90 in the first region M. The interpolation options are discussed below with reference to FIGS. 9, 10 and 11.

Figure 9:
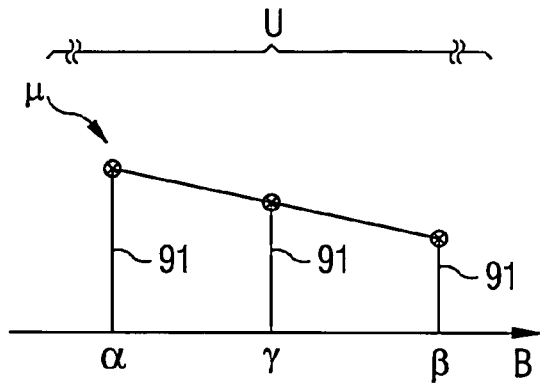
FIG. 9 illustrates the interpolation between adjacent data points of an absorption parameter.
Figure 10:
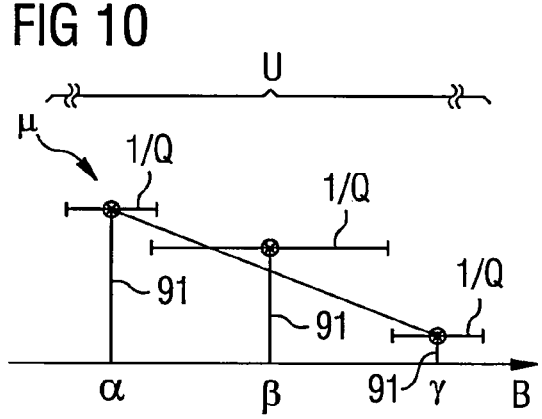
FIG. 10 illustrates the interpolation according to FIG. 9 for absorption parameter values affected by spatial distortion.

FIG. 9 shows a linear interpolation (continuous line) for the locations α and β at which measured second MR data 81 is present and the second value 91 was calculated, such that the second value 91 of the absorption parameter μ at the location γ, which is situated between the locations α and β, can be obtained by way of the interpolation. In FIG. 10, the locations α, β and γ at which the second values 91 of the absorption parameter μ are determined are provided with a certain uncertainty in terms of the location. This uncertainty can arise as a result of distortions of the second MR data 81, as has already been explained hereinabove. This uncertainty is illustrated in FIG. 10 by horizontal error bars. For example, the quality factor Q can be inversely proportional to the uncertainty. Accordingly, the second value 91 of the absorption parameter μ at the location β has a lower quality factor Q than the second values 91 of the absorption parameter μ at the locations α and γ. The second values 91 can be interpolated in such a way that those second values 91 which have a greater quality factor Q or a lower spatial distortion are taken into account to a greater extent. This is indicated graphically in FIG. 10 by the linear interpolation (continuous line) between the locations α, μ and γ, which takes lesser account of the second value 91 of the absorption parameter μ at the location μ.

Figure 11:
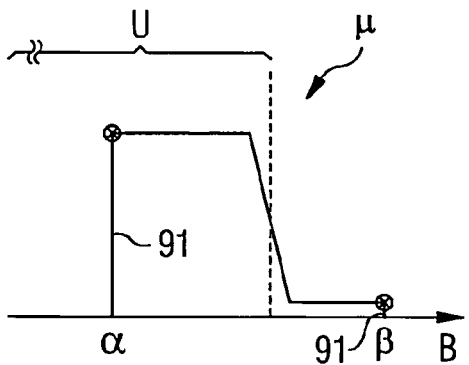
FIG. 11 illustrates the interpolation according to FIG. 9 for absorption parameter values which are located inside and outside an examination object.

It is also possible to take account of outlines of the examination object U in the interpolation of the second values 91. This is illustrated in more detail with reference to FIG. 11. FIG. 11 concerns a case in which the location α lies within the outline of the examination object U, while the location β lies outside. The outline of the examination object U is graphically illustrated in FIG. 11 by a dashed vertical line. The second values 91 are now interpolated (continuous line) between the locations α and β, not in a linear manner as in FIGS. 9 and 10, but taking account of the outlines. For example, as shown in FIG. 11, the transition between the second value 91 of the absorption parameter μ at the location α and the second value 91 at the location β can happen in a step function. Typically, this matches the physical conditions better.

Referring to FIGS. 12 to 18, results of a method according to at least one embodiment of the invention are compared below with conventional methods. FIG. 12 graphically shows PET data 100 in which an attenuation correction has been performed on the basis of an absorption parameter value determined from CT data. FIG. 12 therefore constitutes a reference with conventional methods. CT-based calculation of the attenuation correction parameter value requires the patient to be exposed to a significant dose of radiation. An alternative possibility of performing an attenuation correction is illustrated with reference to FIG. 13. FIG. 13 shows a case in which the attenuation correction has been performed on the basis of a parameter map of the absorption parameter value 90, 91 which was carried out according to the method of Nuyts et al. mentioned in the introduction. In this case only MR data within the field of view of the MR system 5 was acquired. The absorption parameter value 90, 91 for the regions lying outside the field of view has been extracted from the PET data 100 itself. FIG. 14 shows a PET image 100 having an attenuation correction as explained hereinabove with reference to FIGS. 1 to 11.

Figure 16:
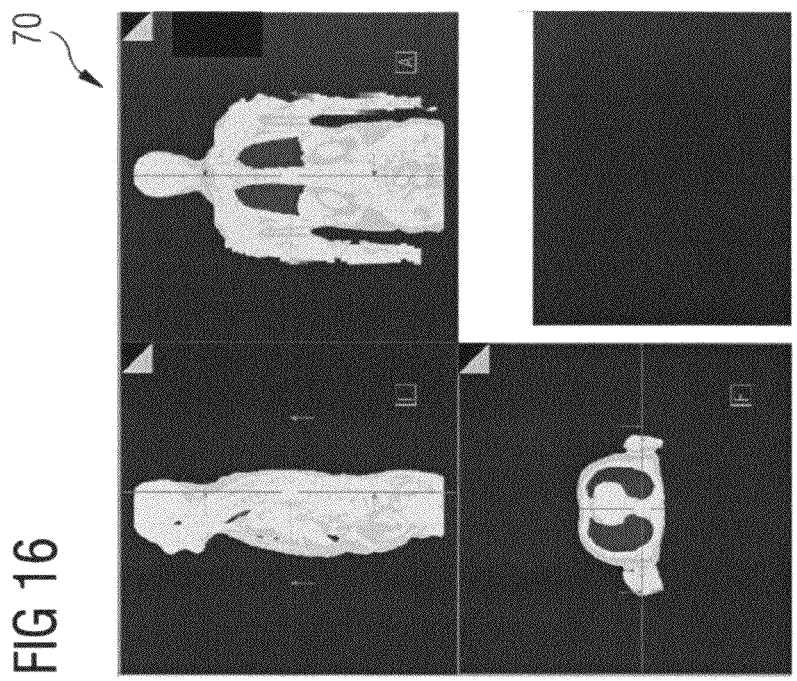
FIG. 16 shows a parameter map calculated from first and second MR data.
Figure 15:
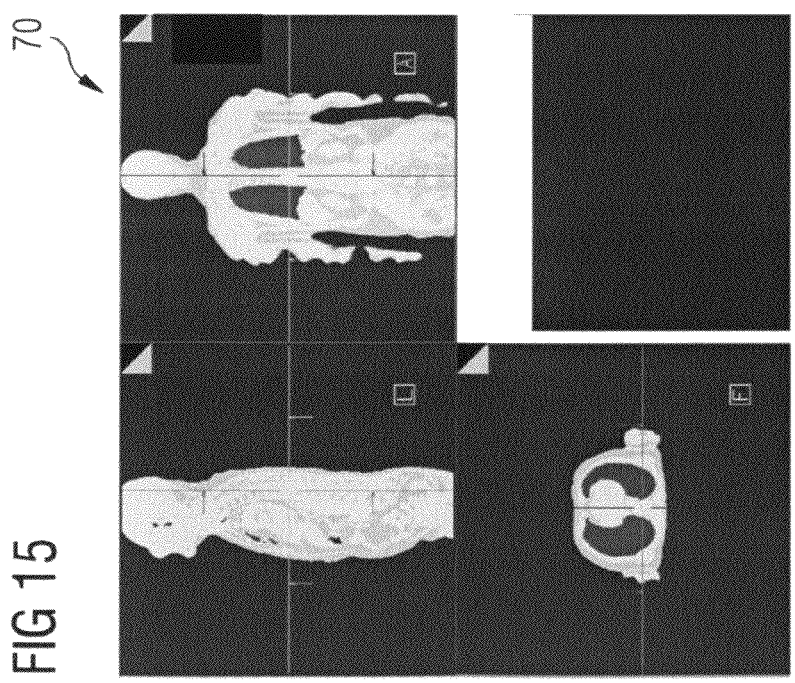
FIG. 15 shows a parameter map calculated from first MR data.

FIGS. 15 and 16 shows the parameter maps 70 in graphically encoded form in different perspectives. FIG. 15 shows a parameter map 70 produced solely on the basis of first MR data 80 acquired within the first region M, i.e. within the field of view of the MR system 5. Correspondingly, FIG. 16 shows a parameter map 70 produced on the basis of first and second MR data 80, 81, as explained hereinabove e.g. with reference to FIG. 3. As is evident from a comparison of FIGS. 16 and 15, the parameter map according to FIG. 16 has an improved acquisition of the absorption parameter value 90, 91 precisely in the peripheral regions e.g. of the arms of the examination subject.

Figure 17:
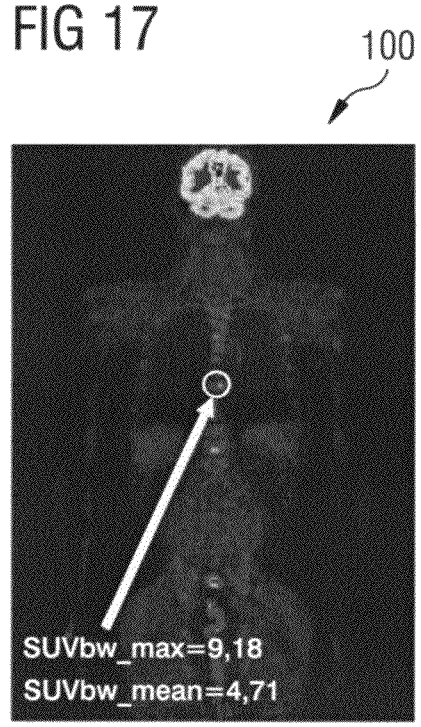
FIG. 17 shows a PET image in which an attenuation correction has been performed on the basis of a parameter map which was obtained only from first MR data.

FIG. 17 shows PET data 100 generated on the basis of the parameter map 70, as illustrated in FIG. 15, i.e. only on the basis of the first MR data 80 in the first region M. As a comparison of FIGS. 17 and 14 reveals, it is important for the accuracy of the PET data to perform an improved attenuation correction on the basis of the parameter map 70 obtained from first and second MR data 80, 81 (see FIG. 16).

Although the invention has been illustrated and described in detail on the basis of the preferred exemplary embodiments, it is not limited by the disclosed examples, and other variations can be derived herefrom by the person skilled in the art without leaving the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for calculating a spatially resolved value of an absorption parameter for a positron emission tomography (PET) scan of an examination object via magnetic resonance tomography, the method comprising:
   acquiring first magnetic resonance (MR) data within a first region during a first measurement operation, the first region lying within a field of view of a magnetic resonance system;
   calculating, via spatial resolution, a first value of the absorption parameter from the first MR data within the first region in order to obtain a three-dimensional (3D) parameter map, the 3D parameter map within the first region including the calculated first value of the absorption parameter in spatially resolved form;
   acquiring second MR data within a second region during a second measurement operation subsequent to the first measurement operation, the second region including the first region and a third region, the third region bordering on the first region in a radial direction and lying at an edge of the field of view;
   calculating, via spatial resolution, a second value of the absorption parameter from the second MR data within the second region; and
   extending the 3D parameter map by the second value of the absorption parameter calculated from the second MR data, the extended 3D parameter map within the first region and the second region including the value of the absorption parameter in spatially resolved form.

2. The method of claim 1, wherein the first MR data within the second region includes greater spatial distortions than the second MR data.

3. The method of claim 2, wherein the second MR data is recorded by way of an MR recording sequence which comprises:
   generation of a gradient field including a nonlinearity of its spatial dependence such that, in the second region, the nonlinearity compensates for a spatial inhomogeneity of a basic magnetic field.

4. The method of claim 1, wherein the second MR data is recorded by way of an MR recording sequence which comprises:
   generation of a gradient field including a nonlinearity of its spatial dependence such that, in the second region, the nonlinearity compensates for a spatial inhomogeneity of a basic magnetic field.

5. The method of claim 1, wherein the first MR data is acquired by way of a Dixon MR recording technique in which the phase angle of the magnetization in fat and water at an echo time instant is used in order to differentiate between fat and water fractions in the examination object.

6. The method of claim 1, wherein the first MR data includes a relatively higher spatial resolution than the second MR data.

7. The method of claim 1, further comprising:
   interpolating the second value of the absorption parameter, calculated from the second MR data, onto the spatial resolution of the first value of the absorption parameter.

8. The method of claim 7, wherein the interpolation within the second region takes outlines of the examination object into account.

9. The method of claim 8, wherein the interpolation additionally comprises:
   weighting, via spatial resolution, the second value of the absorption parameter calculated from the second MR data with a quality factor, wherein the quality factor quantifies a spatial distortion of the second associated MR data and the interpolation takes relatively greater account of second values of the absorption parameter including a relatively higher quality factor.

10. The method of claim 7, wherein the interpolation further comprises:
    weighting, via spatial resolution, the second value of the absorption parameter calculated from the second MR data with a quality factor, wherein the quality factor quantifies a spatial distortion of the second associated MR data and the interpolation takes relatively greater account of second values of the absorption parameter including a relatively higher quality factor.

11. The method of claim 1, further comprising:
    determining a position and an outline of the examination object imaged by way of the second MR data,
    wherein the calculation of the second value of the absorption parameter takes place based on the determined position and outline.

12. The method of claim 11, wherein, for regions of the examination object lying within the determined outline, the calculation includes the assignment of a determined second value of the absorption parameter, and for regions lying outside the determined outline, the calculation includes the assignment of a further determined second value of the absorption parameter.

13. The method of claim 1, further comprising:
acquiring the second MR data within the first region,
segmenting the second MR data into second MR data which, in each case, images the first and the second region, and
discarding the second MR data which images the first region.

14. A method for positron emission tomography, the method comprising:
acquiring PET data; and
correcting the PET data by way of an attenuation correction parameter, wherein the attenuation correction parameter is obtained from a parameter map of a value of an absorption parameter which is obtained via the method of claim 1.

15. A magnetic resonance system, comprising:
a recording device, configured to record MR data of an examination object arranged in a tube of the magnetic resonance system, the recording device being configured to perform,
acquisition of first magnetic resonance (MR) data within a first region during a first measurement operation, the first region lying within a field of view of the magnetic resonance system, and
acquisition of second MR data within a second region during a second measurement operation subsequent to the first measurement operation, the second region including the first region and a third region, the third region bordering on the first region in a radial direction and lying at an edge of the field of view; and
a processor including attached memory, configured to perform,
spatially resolved calculation of a first value of the absorption parameter from the first MR data within the first region to obtain a three-dimensional (3D) parameter map, within the first region, the 3D parameter map including the first value of the absorption parameter in spatially resolved form,
spatially resolved calculation of a second value of the absorption parameter from the second MR data within the second region, and
extension of the 3D parameter map by the second value of the absorption parameter calculated from the second MR data such that, within the first region and the second region, the extended 3D parameter map includes the value of the absorption parameter in spatially resolved form.

16. The magnetic resonance system of claim 15, wherein the examination object is a human examination subject and the arms of the examination subject are arranged within the second region.

17. The magnetic resonance system of claim 16, wherein the first region extends in the radial direction inside a first radius in relation to a central axis of the tube and the second region extends in the radial direction between the first radius and a second radius in relation to the central axis, wherein the second radius is relatively greater than the first radius.

18. The magnetic resonance system of claim 15, wherein the first region extends in the radial direction inside a first radius in relation to a central axis of the tube and the second region extends in the radial direction between the first radius and a second radius in relation to the central axis, wherein the second radius is relatively greater than the first radius.

19. A positron emission tomograph, comprising:
a recording device, configured to acquire PET data; and
a processor, configured to correct the PET data by way of an attenuation correction parameter, wherein the attenuation correction parameter is obtained from a parameter map of a value of an absorption parameter which is obtained via the method of claim 1.

20. A non-transitory computer readable medium including program segments for, when executed on a computer device, causing the computer device to implement the method of claim 1.

21. A non-transitory computer readable medium including program segments for, when executed on a computer device, causing the computer device to implement the method of claim 14.

* * * * *